US012600741B2

(12) United States Patent
Yun et al.

(10) Patent No.: US 12,600,741 B2
(45) Date of Patent: Apr. 14, 2026

(54) 3-PHENOXYBENZOIC ACID-GLUCURONIC ACID CONJUGATE, AND PREPARATION METHOD AND USE THEREOF

(71) Applicant: Shanxi Medical University, Jinzhong (CN)

(72) Inventors: Keming Yun, Jinzhong (CN); Zhuoyi Wang, Jinzhong (CN); Ying Wang, Jinzhong (CN); Yuping Lu, Jinzhong (CN); Xianlian Wang, Jinzhong (CN); Hongliang Su, Jinzhong (CN); Chao Zhang, Jinzhong (CN); Zhiwen Wei, Jinzhong (CN); Lele Wang, Jinzhong (CN); Ruili Wang, Jinzhong (CN)

(73) Assignee: Shanxi Medical University, Jinzhong (CN)

( * ) Notice: Subject to any disclaimer, the term of this patent is extended or adjusted under 35 U.S.C. 154(b) by 463 days.

(21) Appl. No.: 18/192,609

(22) Filed: Mar. 29, 2023

(65) Prior Publication Data

US 2024/0287119 A1 Aug. 29, 2024

(30) Foreign Application Priority Data

Feb. 17, 2023 (CN) ......................... 202310149979.8

(51) Int. Cl.

| | |
|---|---|
| ***C07H 13/08*** | (2006.01) |
| ***B01J 21/18*** | (2006.01) |
| ***B01J 23/44*** | (2006.01) |
| ***C07H 15/203*** | (2006.01) |
| ***G01N 33/53*** | (2006.01) |

(52) U.S. Cl.

CPC ............ *C07H 15/203* (2013.01); *B01J 21/18* (2013.01); *B01J 23/44* (2013.01); *C07H 13/08* (2013.01); *G01N 33/5308* (2013.01); *G01N 2800/42* (2013.01)

(58) Field of Classification Search

None

See application file for complete search history.

(56) References Cited

PUBLICATIONS

Noort et al., Chemical Research in Toxicology, vol. 21 (7), Jul. 21, 2008, pp. 1396-1406. (Year: 2008).*

* cited by examiner

*Primary Examiner* — Traviss C McIntosh, III

(74) *Attorney, Agent, or Firm* — Straylight LLP

(57) ABSTRACT

The present disclosure provides a 3-phenoxybenzoic acid-glucuronic acid conjugate, and a preparation method and use thereof, and belongs to the technical field of pesticide detection. Compared with 3-phenoxybenzoic acid, the 3-phenoxybenzoic acid-glucuronic acid conjugate provided by the present disclosure features structural stability, high specificity, long limit of detection, and high content in urine, and can better serve as a marker that identifies whether an organism is killed due to pyrethroid pesticide poisoning. Namely, the 3-phenoxybenzoic acid-glucuronic acid conjugate can detect whether a toxicant (pyrethroid pesticides) is taken antemortem or exposed postmortem, and has an excellent application prospect in pyrethroid pesticide detection. The present disclosure provides a preparation method of a 3-phenoxybenzoic acid-glucuronic acid conjugate. The preparation method provided by the present disclosure features high product yield, simple operation, wide raw material sources, low costs, and suitability for industrial production.

13 Claims, 9 Drawing Sheets

UV chromatogram 2

Total ion chromatogram in anionic mode

3-PHENOXYBENZOIC ACID-GLUCURONIC ACID CONJUGATE, AND PREPARATION METHOD AND USE THEREOF

CROSS REFERENCE TO RELATED APPLICATION

This patent application claims the benefit and priority of Chinese Patent Application No. 202310149979.8, filed with the China National Intellectual Property Administration on Feb. 17, 2023, the disclosure of which is incorporated by reference herein in its entirety as part of the present application.

TECHNICAL FIELD

The present disclosure relates to the technical field of pesticide detection, in particular to a 3-phenoxybenzoic acid-glucuronic acid conjugate, and a preparation method and use thereof.

BACKGROUND

Pyrethroids are a class of biomimetically synthesized broad-spectrum pesticides that can control a plurality of insect pests, and features high efficiency, low toxicity, and fast rate of biodegradation. In recent years, because of full delisting of high-toxic pesticides, agricultural market in China has an increasing demand for pyrethroid insecticides with high efficiency, low toxicity, and low residue. Pyrethroid insecticides occasionally lead to accidental poisoning and oral poisoning suicides due to large-scale application, wide application area, and more exposed population thereof. Therefore, forensic identification and examination of pyrethroid pesticide poisoning have become one of the important contents of forensic toxicology. It was found that fenpropathrin was mainly distributed in postmortem rabbit and dog livers, kidneys, lungs, and other tissues rich in blood flow, and it was found in the blood and livers of preserved specimens that fenpropathrin was decomposed over time. The results of the influence of thermal decomposition kinetics in buried cadavers showed that: the content of fenpropathrin first increased and then decreased in viscera of cadavers. It was further found in research on forensic toxicokinetics of cypermethrin and fenvalerate that the possibility of postmortem distribution was very high and there were differences in distribution of toxicants in viscera because of high liposolubility of these substances. Therefore, during the expertise of cases of pyrethroid poisoning, the poisoning cannot be simply determined depending on the protomer content, and the determination of antemortem markers in vivo of these toxicants is of great significance to the forensic toxicological analysis.

Foreign toxicants undergo a series of metabolic reactions and are eliminated from the body after entry into the body. Metabolic reactions mainly include two types: phase I and II metabolisms. Of them, phase I metabolism is a series of oxidation, reduction and hydrolysis reactions mediated by the hepatic microsomal enzyme P450 family; phase II metabolism is a conjugation reaction, including sulfation, glucuronidation, and conjugation with glutathione. Current research shows that poisonous pyrethroid insecticides are metabolized rapidly in animals, and the ester bond cleavage mainly occurs in these compounds. Herein, 3-phenoxybenzoic acid (3-PBA) is a non-specific phase I metabolite of these poisons. For example, in terms of fenpropathrin, cypermethrin, deltamethrin, and fenvalerate, the phase I metabolic process of pyrethroid insecticides is as follows:

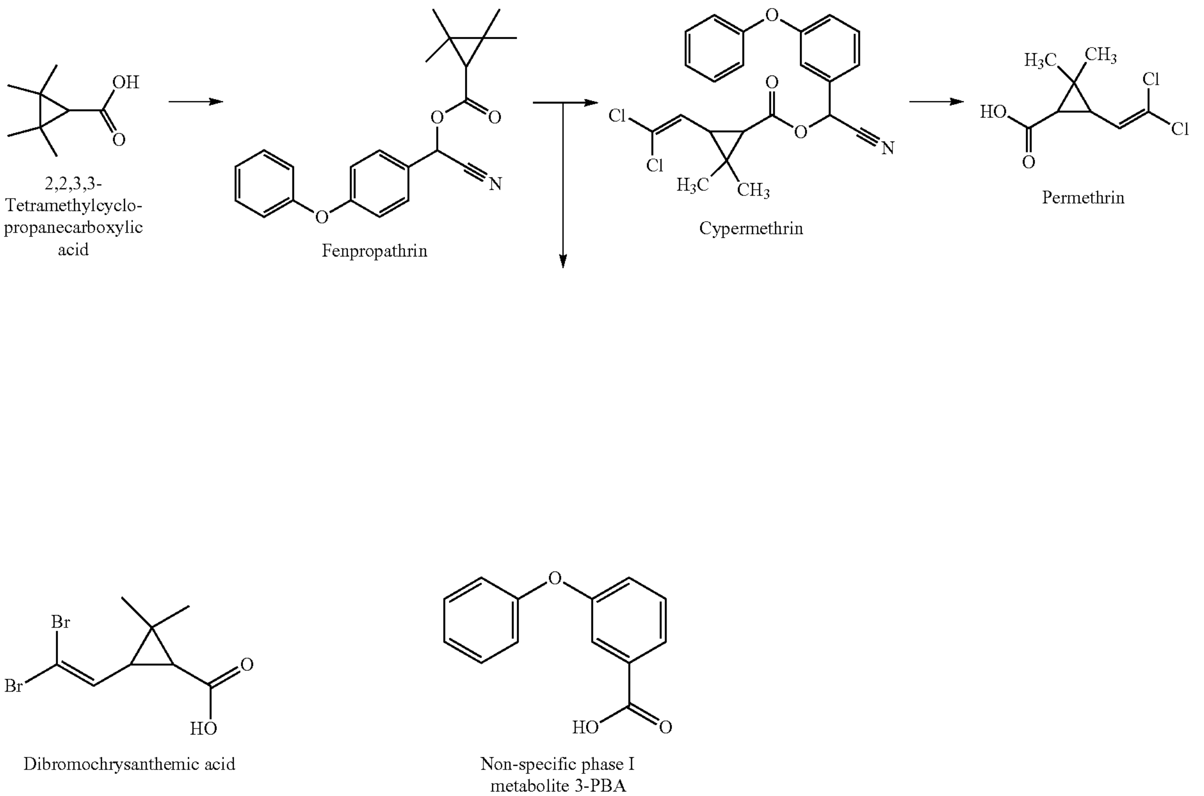

2,2,3,3-Tetramethylcyclopropanecarboxylic acid

Fenpropathrin

Cypermethrin

Permethrin

Dibromochrysanthemic acid

Non-specific phase I metabolite 3-PBA

-continued

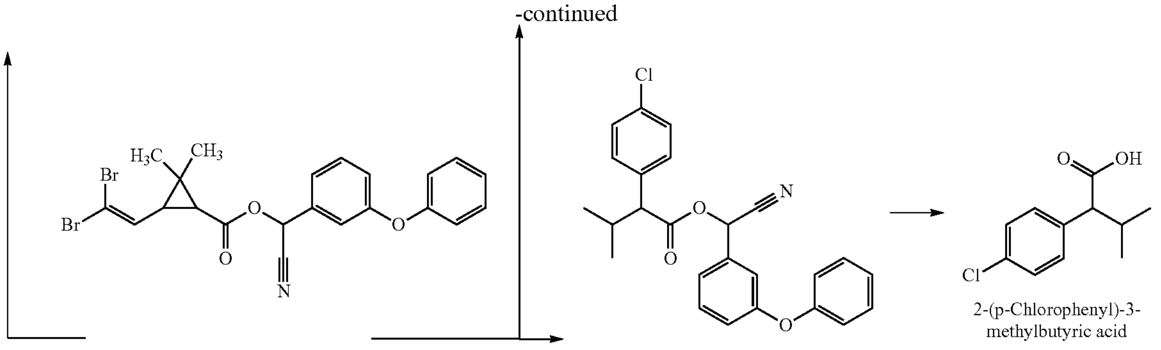

Dibromochrysanthemic acid

Fenvalerate 2-(p-Chlorophenyl)-3-methylbutyric acid

At present, in forensic practice, it is necessary to identify whether pyrethroid pesticides are taken antemortem or exposed postmortem, forensic toxicokinetics is an important means to solve the problem of whether a toxicant is taken antemortem or exposed postmortem, and protomers and phase I metabolites of pyrethroid insecticides are mainly detected. However, both protomers and phase I metabolites of pyrethroid insecticides have poor stability, leading to short detection time. Thus, detection results cannot determine whether an organism is killed due to pyrethroid insecticide poisoning.

SUMMARY

In view of this, an objective of the present disclosure is to provide a 3-phenoxybenzoic acid-glucuronic acid conjugate, and a preparation method and use thereof. The 3-phenoxybenzoic acid-glucuronic acid conjugate provided by the present disclosure features structural stability, high specificity, long elimination half-life in human blood and urine, and long limit of detection, and can better identify whether an organism is killed due to pyrethroid pesticide poisoning.

To achieve the above objective, the present disclosure provides the following technical solutions:

The present disclosure provides a 3-phenoxybenzoic acid-glucuronic acid conjugate, having a structure represented b formula I:

formula I

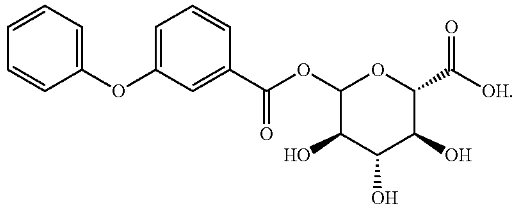

The present disclosure provides a preparation method of the 3-phenoxybenzoic acid-glucuronic acid conjugate according to the above technical solution, including the following steps:

mixing a compound II, a compound III, an organic base, and a coupling reagent with a first organic solvent to conduct a condensation reaction to yield a compound IV; and mixing the compound IV with a hydrogenation catalyst and a second organic solvent to conduct a hydrogenation reaction in a hydrogen-atmosphere to yield the 3-phenoxybenzoic acid-glucuronic acid conjugate;

Compound II

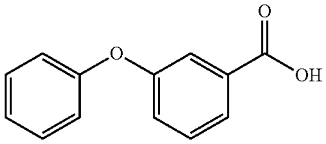

Compound III

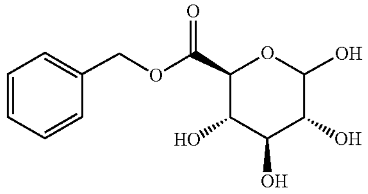

Compound IV

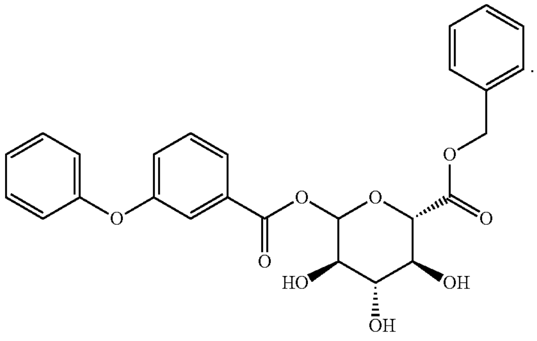

Preferably, the compound II and the compound II may have a molar ratio of 1:(0.3-3).

Preferably, the coupling reagent may be at least one selected from the group consisting of 2-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU), N-(3-dimethylaminopropyl)-N'-ethylcarbodiimide hydrochloride, and 1-hydroxybenzotriazole.

Preferably, the first organic solvent may be at least one selected from the group consisting of nitrile-based solvents, furan-based solvents, pyridine-based solvents, acyl-based solvents, and alkylogen solvents.

Preferably, the condensation reaction may be conducted at a temperature of −10 to 80° C. for 0.5-48 h.

Preferably, the hydrogenation catalyst may be at least one selected from the group consisting of palladium on carbon, palladium hydroxide, and platinum oxide.

Preferably, the second organic solvent may be at least one selected from the group consisting of alcoholic solvents, ester solvents, and alkylogen solvents.

Preferably, the hydrogenation reaction may be conducted at a temperature of 0-80° C. for 1-48 h, and hydrogen pressure may be 0.1-3 MPa.

The present disclosure provides use of the 3-phenoxybenzoic acid-glucuronic acid conjugate according to the above technical solution or a 3-phenoxybenzoic acid-glucuronic acid conjugate prepared by the preparation method according to the above technical solution as a standard compound in detecting pyrethroid pesticides.

The present disclosure provides a 3-phenoxybenzoic acid-glucuronic acid conjugate. The 3-phenoxybenzoic acid-glucuronic acid conjugate provided by the present disclosure (hereinafter referred to as compound TM1) is a phase II metabolite of pyrethroid pesticides. Compared with 3-phenoxybenzoic acid (3-PBA), the compound TM1 has stronger specificity, higher structural stability, and longer elimination half-life in human blood and urine, and substantially increases the detection time of the pyrethroid pesticides. Moreover, the compound TM1 has high content in urine, and can better serve as a marker that identifies whether an organism is killed due to pyrethroid pesticide poisoning. Namely, the compound TM1 can detect whether a toxicant (pyrethroid pesticides) is taken antemortem or exposed postmortem, and has an excellent application prospect in pyrethroid pesticide detection.

The present disclosure provides a preparation method of the 3-phenoxybenzoic acid-glucuronic acid conjugate according to the above technical solution. The preparation method provided by the present disclosure features high product yield, simple operation, wide raw material sources, low costs, and suitability for industrial production.

DETAILED DESCRIPTION OF THE EMBODIMENTS

Figure 1:
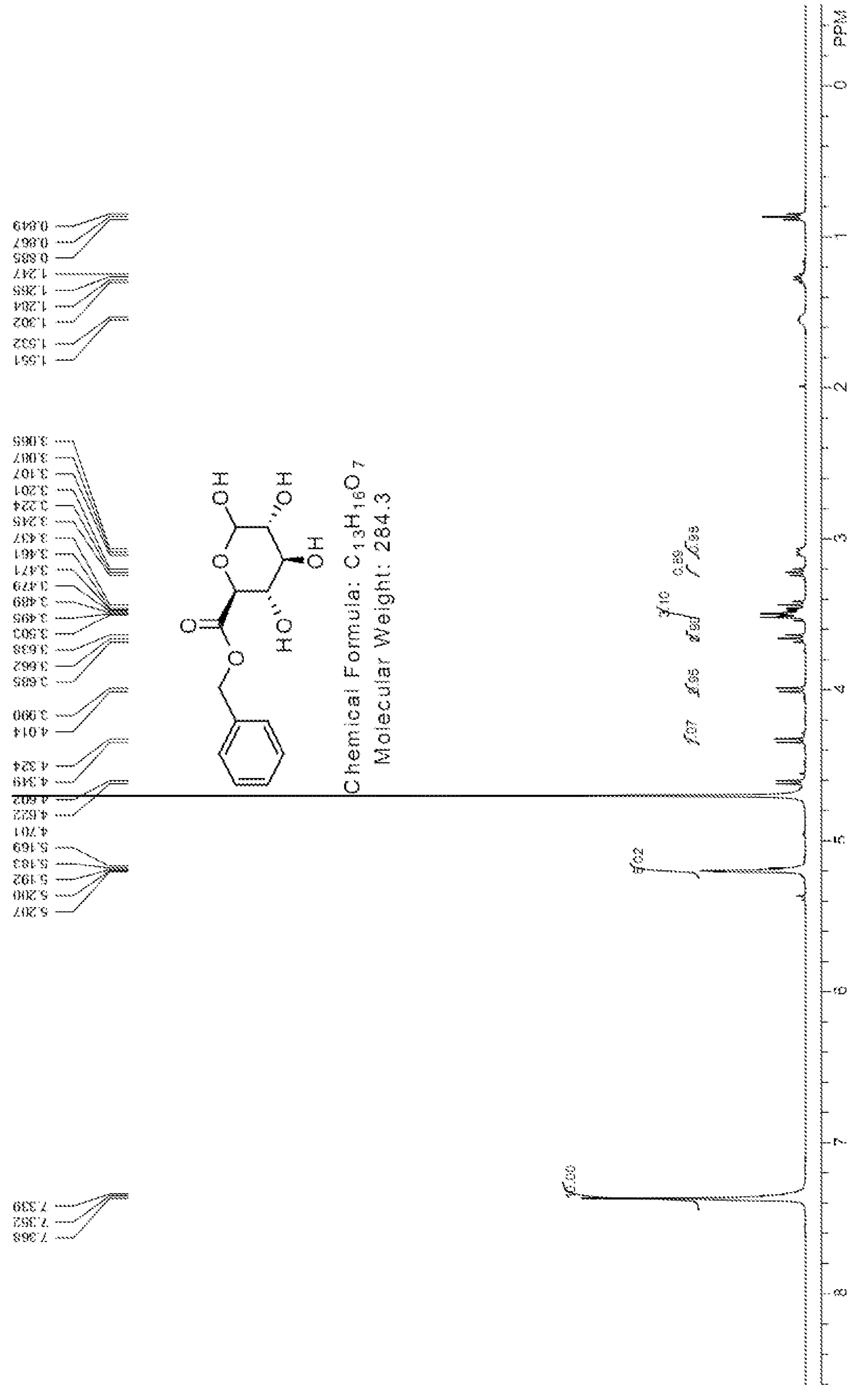
FIG. 1 shows a $^1$H NMR spectrogram of a compound III.

The present disclosure provides a 3-phenoxybenzoic acid-glucuronic acid conjugate, having a structure represented by formula I:

formula I

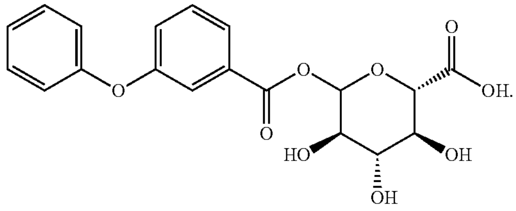

In the present disclosure, unless otherwise specified, all raw material components are commercially available products well known to those skilled in the art.

The present disclosure provides a preparation method of the 3-phenoxybenzoic acid-glucuronic acid conjugate according to the above technical solution, including the following steps:

mixing a compound II, a compound III, an organic base, and a coupling reagent with a first organic solvent to conduct a condensation reaction to yield a compound IV; and mixing the compound IV with a hydrogenation catalyst and a second organic solvent to conduct a hydrogenation reaction in a hydrogen-atmosphere to yield the 3-phenoxybenzoic acid-glucuronic acid conjugate;

Compound II

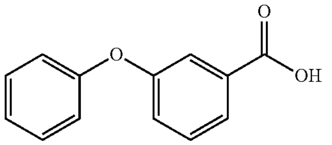

Compound III

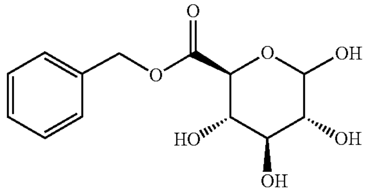

Compound IV

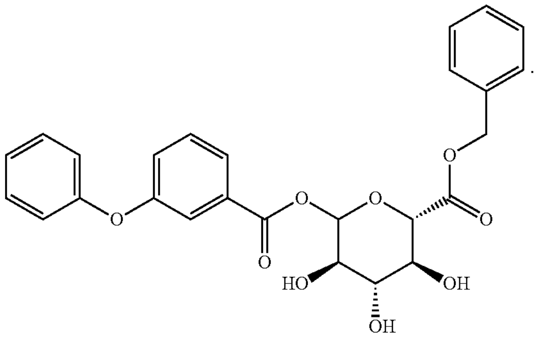

In the present disclosure, a compound II, a compound Ill, an organic base, and a coupling reagent are mixed with a first organic solvent to conduct a condensation reaction to yield a compound IV.

In the present disclosure, a preparation method of a compound 1 may preferably include the following step: mixing the compound II, tetrabutylammonium fluoride (TBAF), and benzyl bromide (BnBr) with an organic solvent (labeled as a third organic solvent) to conduct a substitution reaction to yield the compound III;

compound 1

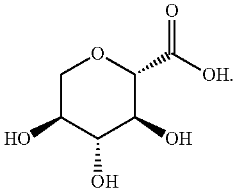

In the present disclosure, the compound 1 and the BnBr may preferably have a molar ratio of 1:(0.5-3.0), more preferably 1:(1-2), and further preferably 1:(1.05-1.5). In the present disclosure, the compound 1 and the TBAF may preferably have a molar ratio of 1:(0.5-3.0), more preferably 1:(1-2), and further preferably 1:(1.1-1.5). In the present disclosure, the third organic solvent may preferably include an amide solvent, and more preferably N,N-dimethylformamide (DMF). The present disclosure has no particular limitation on a volume of the third organic solvent, as long as the volume may ensure the successful conduct of the substitution reaction.

The present disclosure has no particular limitation on a method for the mixing, as long as raw materials may be mixed well, specifically, for example, stirring mixing. In the specific examples of the present disclosure, the mixing may preferably be implemented as follows: mixing a solution of the compound 1 with a TBAF solution at room temperature, and mixing a resulting mixed solution with the BnBr at −10 to 50° C. (more preferably −5 to 25° C., and further preferably 0° C.). In the present disclosure, the solution of the compound 1 may preferably have a concentration of 0.01-2 mol/L, more preferably 0.5-1.5 mol/L, and further preferably 0.515 mol/L. In the present disclosure, the TBAF solution may preferably have a concentration of 0.01-10.0 mol/L, more preferably 0.5-5 mol/L, and further preferably 1-2 mol/L.

In the present disclosure, the substitution reaction may preferably be conducted at room temperature for 0.5-48 h, more preferably 5-30 h, and further preferably 10-15 h. In the present disclosure, a reaction occurred during the substitution reaction is represented by formula (1):

formula (1)

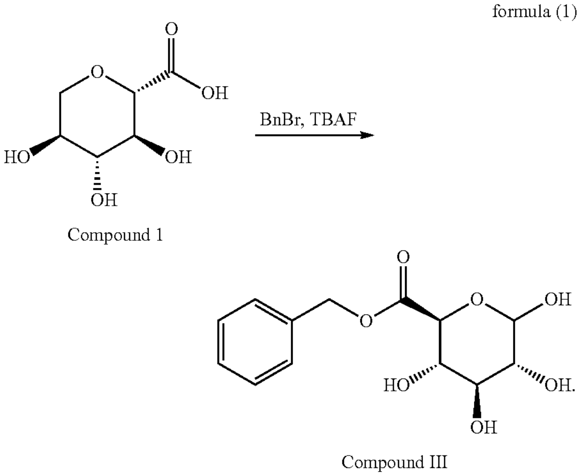

Compound 1

Compound III

After the substitution reaction is completed, the present disclosure may further preferably include concentration of a resulting substitution reaction mixture and purification by silica gel column chromatography to yield the compound III. The present disclosure has no particular limitation on the concentration, as long as a concentration method well known to those skilled in the art may be adopted to remove the third organic solvent. In the present disclosure, an eluant used in the purification by silica gel column chromatography may preferably include an ethyl acetate-petroleum ether solvent mixture or a methanol-dichloromethane solvent mixture. Ethyl acetate and petroleum ether in the ethyl acetate-petroleum ether solvent mixture may preferably have a volume ratio of 1:(50-0.1), and more preferably 1:(10-0.5). Methanol and dichloromethane in the methanol-dichloromethane solvent mixture may preferably have a volume ratio of 1:(100-0.01), and more preferably 1:(1-0.1).

In the present disclosure, after the compound III is obtained, the compound II, the compound III, the organic base, and the coupling reagent are mixed with the first organic solvent to conduct the condensation reaction to yield the compound IV.

In the present disclosure, the compound II and the compound III may preferably have a molar ratio of 1:(0.3-3), more preferably 1:(0.5-2), and further preferably 1:(0.8-1.5). In the present disclosure, the organic base may preferably be at least one selected from the group consisting of 4-methylmorpholine, triethylamine, diisopropylethylamine (DIPEA), and N,N-dimethylpyridine. The compound II and the organic base may preferably have a molar ratio of 1:(1-3), more preferably 1:(1.5-2.5), and further preferably 1:2. In the present disclosure, the coupling reagent may preferably be at least one selected from the group consisting of 2-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU), N-(3-dimethylaminopropyl)-N'-ethylcarbodiimide hydrochloride, and 1-hydroxybenzotriazole. The compound II and the coupling reagent may preferably have a molar ratio of 1:(0.5-5), more preferably 1:(1-3), and further preferably 1:2.

In the present disclosure, the first organic solvent may be at least one selected from the group consisting of nitrile-based solvents, furan-based solvents, pyridine-based solvents, acyl-based solvents, and alkylogen solvents, and more preferably at least one selected from the group consisting of acetonitrile (ACN), tetrahydrofuran (THF), pyridine, DMF, N,N-dimethylacetamide (DMA), and dichloromethane (DCM). The present disclosure has no particular limitation on a volume of the first organic solvent, as long as the volume may ensure the successful conduct of the condensation reaction.

The present disclosure has no particular limitation on a method for the mixing, as long as raw materials may be mixed well, specifically, for example, stirring mixing; and the mixing may preferably be conducted at room temperature. In the specific examples of the present disclosure, the mixing may preferably be implemented as follows: dissolving the organic base in the first organic solvent to obtain an organic base solution; and mixing the compound II, the compound III, and the organic base solution with the coupling reagent.

In the present disclosure, the condensation reaction may preferably be conducted at −10 to 80° C., more preferably 10 to 40° C., and further preferably room temperature; and the condensation reaction may preferably be conducted for 0.5-48 h, more preferably 5-30 h, and further preferably 8-15 h. In the present disclosure, a reaction occurred during the condensation reaction is represented by formula (2):

formula (2)

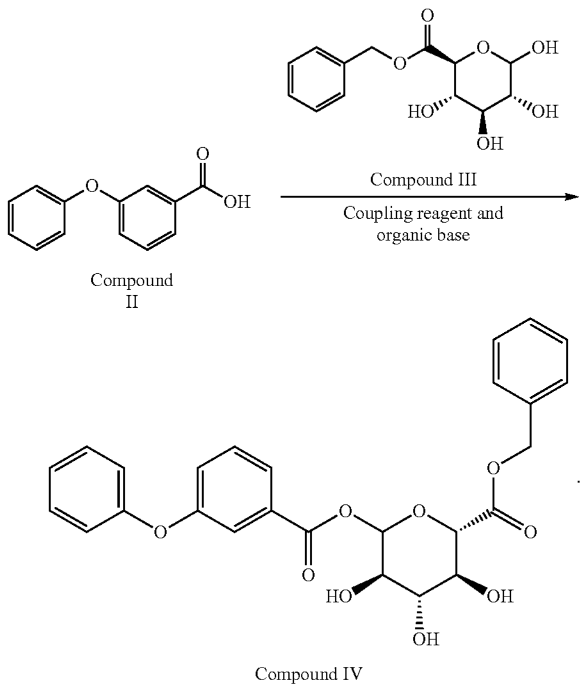

Compound III
Compound II
Compound IV

After the condensation reaction is completed, the present disclosure may further preferably include mixing a resulting condensation reaction mixture with water, organic solvent extraction, washing a resulting organic phase with saturated brine, drying over a desiccant, concentration, and purification by silica gel column chromatography to yield the compound IV successively. In the present disclosure, an organic solvent used in the extraction may preferably be at least one selected from the group consisting of ethyl acetate, DCM, and methyltetrahydrofuran. In the present disclosure, the desiccant may preferably include anhydrous sodium sulfate and/or anhydrous magnesium sulfate. The present disclosure has no particular limitation on the concentration, as long as a concentration method well known to those skilled in the art may be adopted to remove the solvent. In the present disclosure, the eluant used in the purification by silica gel column chromatography may preferably include a petroleum ether-ethyl acetate solvent mixture, and petroleum ether and ethyl acetate in the petroleum ether-ethyl acetate solvent mixture may preferably have a volume ratio of 5:1 to 1:5, and more preferably 3:1 to 1:3.

In the present disclosure, after the compound IV is obtained, the compound IV is mixed with the hydrogenation catalyst and the second organic solvent to conduct the hydrogenation reaction in a hydrogen-atmosphere to yield the 3-phenoxybenzoic acid-glucuronic acid conjugate.

In the present disclosure, the hydrogenation catalyst may preferably be at least one selected from the group consisting of palladium on carbon, palladium hydroxide, and platinum oxide. In the present disclosure, the compound IV and the hydrogenation catalyst may preferably have a mass ratio of (1-20):1, more preferably (3-15):1, and further preferably (5-10):1.

In the present disclosure, the second organic solvent may preferably be at least one selected from the group consisting of alcoholic solvents, ester solvents, and alkylogen solvents, and more preferably at least one selected from the group consisting of methanol (MeOH), ethanol, ethyl acetate, and DCM. The present disclosure has no particular limitation on a volume of the second organic solvent, as long as the volume may ensure the successful conduct of the hydrogenation reaction.

In the present disclosure, the hydrogenation reaction may preferably be conducted at 0 to 80° C., more preferably 10 to 40° C., and further preferably room temperature; and the hydrogenation reaction may preferably be conducted for 1-48 h, more preferably 5-30 h, and further preferably 8-15 h; hydrogen pressure may preferably be 0.1-3 MPa, more preferably 0.5-2.5 MPa, and further preferably 1-2 MPa. In the present disclosure, a reaction occurred during the hydrogenation reaction is represented by formula (3):

formula (3)

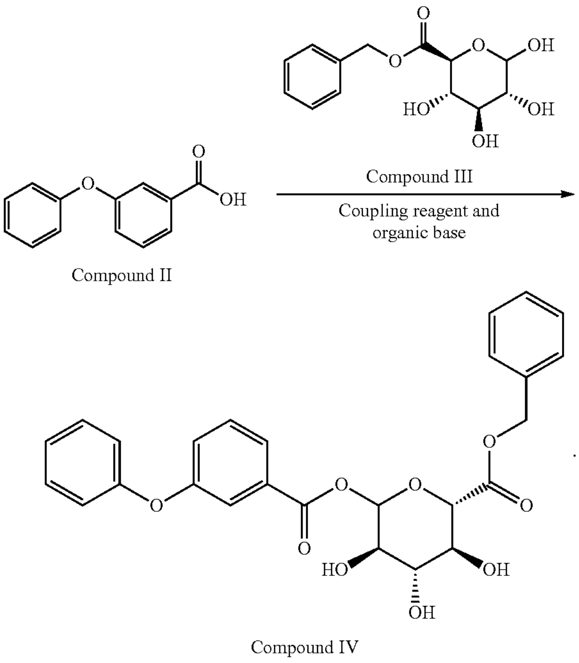

Compound III
Compound II
Compound IV

The present disclosure provides use of the 3-phenoxybenzoic acid-glucuronic acid conjugate according to the above technical solution or a 3-phenoxybenzoic acid-glucuronic acid conjugate prepared by the preparation method according to the above technical solution as a standard compound in detecting pyrethroid pesticides. Compared with 3-phenoxybenzoic acid, the 3-phenoxybenzoic acid-glucuronic acid conjugate provided by the present disclosure features structural stability, high specificity, long elimination half-life in human blood and urine, long limit of detection, and high content in urine, and can better serve as a marker that identifies whether an organism is killed due to pyrethroid pesticide poisoning. Namely, the 3-phenoxybenzoic acid-glucuronic acid conjugate can detect whether a toxicant (pyrethroid pesticides) is taken antemortem or exposed postmortem, and has an excellent application prospect in pyrethroid pesticide detection.

The technical solutions of the present disclosure will be clearly and completely described below with reference to the examples of the present disclosure. Apparently, the described examples are only a part of, not all of, the examples of the present disclosure. Based on the examples of the present disclosure, all other examples obtained by those of ordinary skill in the art without creative efforts shall fall within the protection scope of the present disclosure.

Example 1

At room temperature, TBAF (55 mL, 1 mol/L, 56.6 mmol, 1.1 eq) was added to a solution of compound 1 (10.0 g, 51.5 mmol, 1.0 eq), and BnBr (6.4 mL, 54.1 mmol, 1.05 eq) was added at 0° C.; the resulting mixture was stirred for 12 h at room temperature, concentrated to remove the solvent, and purified by silica gel column chromatography (the eluant was DCM:MeOH (v:v=1:0.1)) to yield compound III (white solid, 12 g, yield 75%). FIG. 1 shows a $^1$H NMR spectrogram of the compound III.

At room temperature, HATU (24.0 g, 63.4 mmol, 1.5 eq) was added to compound II (12.0 g, 42.3 mmol, 1.0 eq), compound III (8.1 g, 38.0 mmol, 0.9 eq) and 4-methylmorpholine (8.5 g, 84.5 mmol, 2.0 eq) in ACN (250 mL); the resulting mixture was stirred at room temperature to react for 12 h, poured into the water to mix well, and extracted with ethyl acetate; the resulting organic phase was successively washed with saturated brine, dried over $Na_2SO_4$, concentrated, and purified by silica gel column chromatography (the volume ratio of petroleum ether/ethyl acetate=1/1) to yield compound IV (white solid, 9 g, yield 45%).

Figure 2:
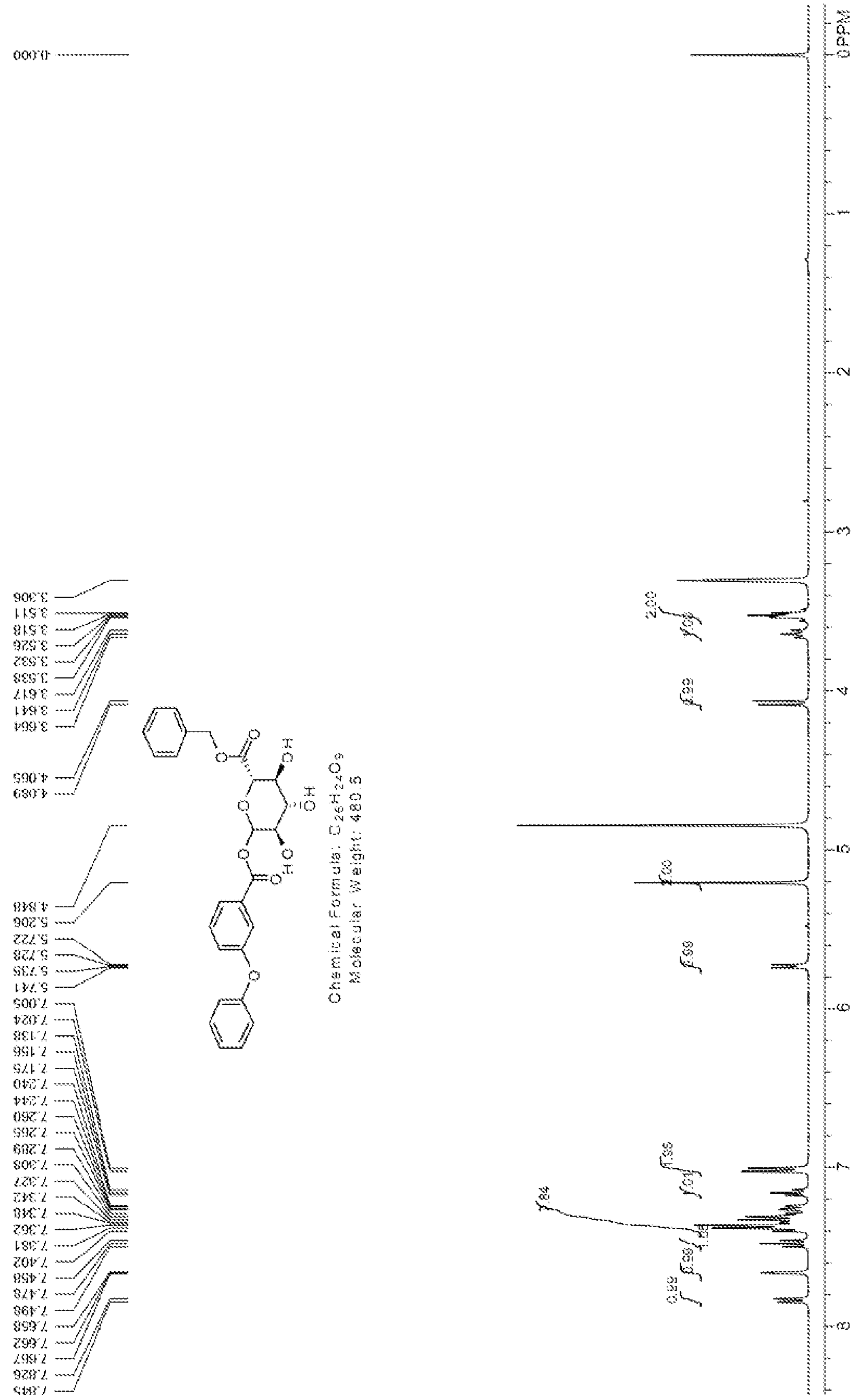
FIG. 2 shows a $^1$H NMR spectrogram of a compound IV.

The $^1$H NMR spectrogram of the compound IV is shown in FIG. 2, and the $^1$H NMR data are as follows: $^1$H NMR (400 MHz, MeOD) δ:7.83 (d, J=7.6 Hz, 1H), 7.66 (t, J=2.0 Hz, 1H), 7.47 (t, J=8.0 Hz, 1H), 7.40-7.24 (m, 8H), 7.15 (t, J=7.6 Hz, 1H), 7.02 (d, J=7.6 Hz, 2H), 5.73 (dd. J=2.0, 5.2 Hz, 1H), 5.20 (s, 2H), 4.07 (d, J=8.8 Hz, 1H), 3.64 (t, J=9.2 Hz, 1H), 3.53-3.51 (m, 2H).

The compound IV (5.0 g, 10.4 mmol, 1.0 eq) and Pd/C (1 g) were mixed in MeOH (100 mL), $H_2$ (the $H_2$ pressure was 0.3 MPa) passed at room temperature, and the resulting mixture was subjected to hydrogenation reaction for 12 h at room temperature under stirring; after filtration, the resulting filtrate was concentrated to a constant weight to yield a 3-phenoxybenzoic acid-glucuronic acid conjugate (hereinafter referred to as TM1, white solid, 4 g, yield 98%).

Figure 3:
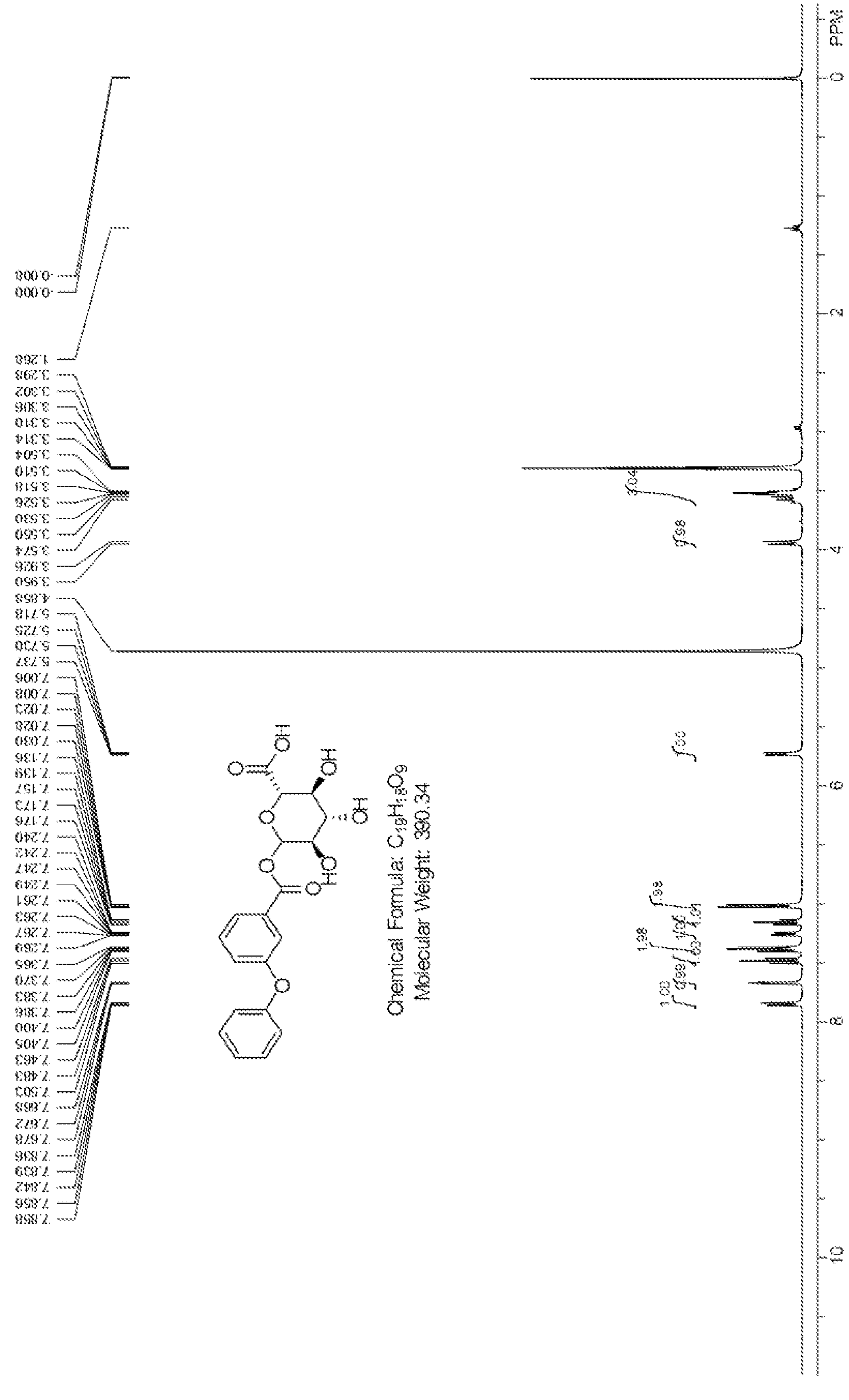
FIG. 3 shows a $^1$H NMR spectrogram of compound TM1.

The $^1$H NMR spectrogram of the compound TM1 is shown in FIG. 3, and the $^1$H NMR data are as follows: $^1$H NMR (400 MHz, MeOD) δ: 7.84 (dd, J=0.8, 6.4 Hz, 1H), 7.66 (dd, J=2.4, 4.0 Hz, 1H), 7.48 (d, J=8.0 Hz, 1H), 7.40-7.36 (m, 2H), 7.27-7.24 (m, 1H), 7.17-7.13 (m, 1H), 7.03-7.00 (m, 2H), 5.72 (dd, J=2.8, 4.8 Hz, 1H), 3.94 (d, J=9.6 Hz, 1H), and 3.57-3.50 (m, 3H).

Figure 4A:
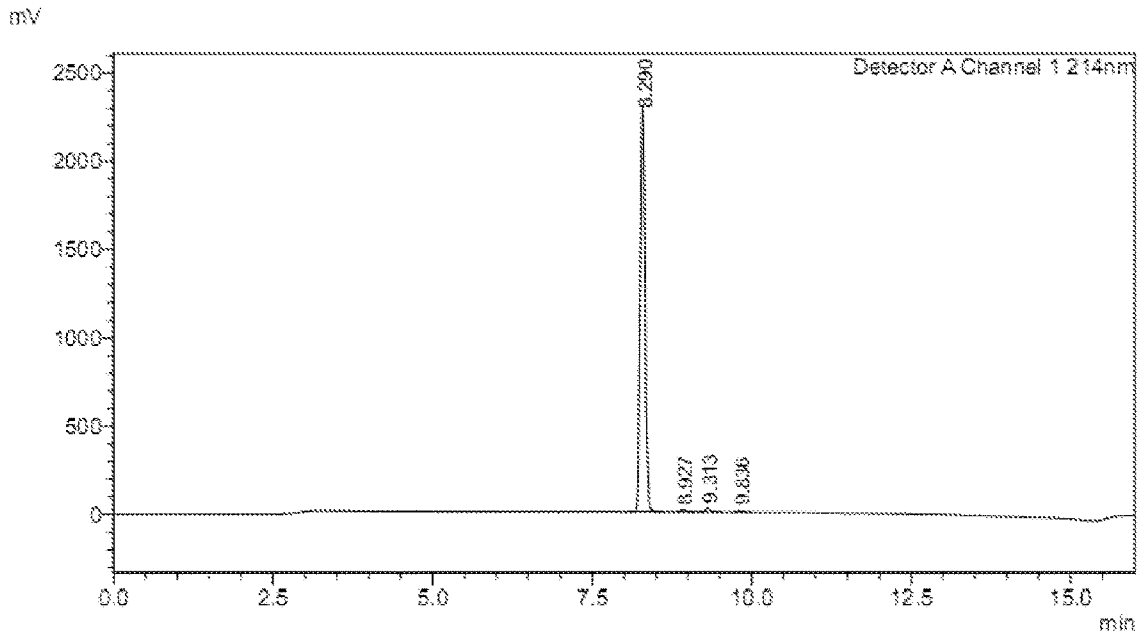
FIG. 4A-B show HPLC chromatograms of compound TM1 at two detection wavelengths (254 nm and 214 nm)
Figure 4B:
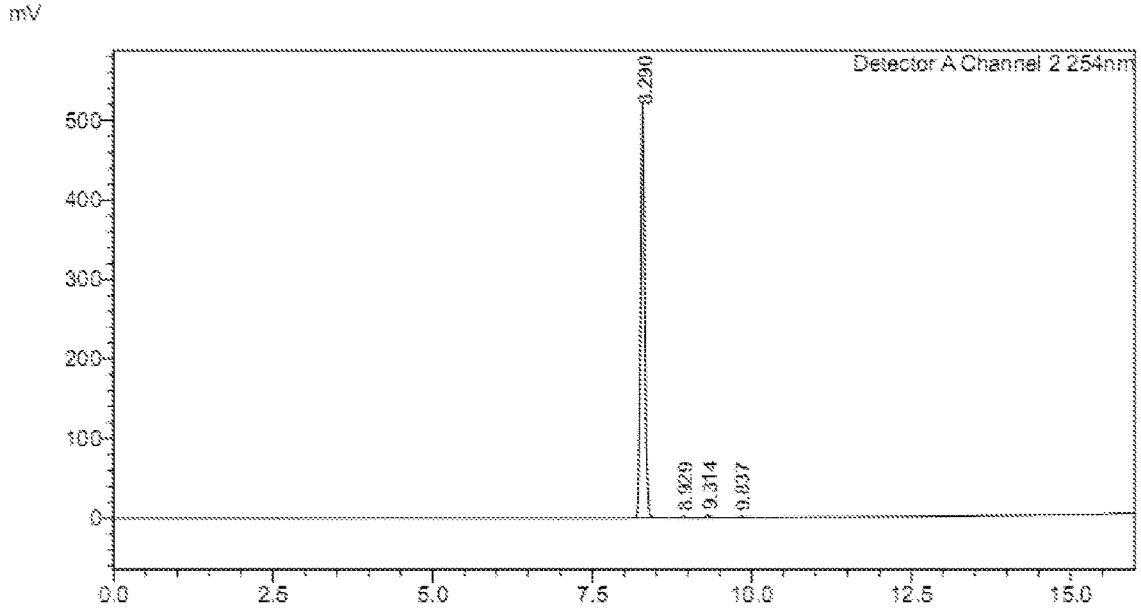

FIG. 4A-B show HPLC chromatograms of compound TM1 at two detection wavelengths (214 nm and 254 nm), and the HPLC data are shown in Tables 1 and 2. Herein, HPLC conditions were as follows: the chromatographic column was SunFire C18 (5 μm, 4.6×150 mm), the flow rate of mobile phase was 1.000 mL/min, the run time was 16 min, the mobile phase A was 0.03 v/v % TFA aqueous solution, and the mobile phase B was 0.03 v/v % TFA in ACN.

TABLE 1

The HPLC data at 214 nm

| Peak# | Ret. Time | USP Width | Height | Area | S/N | Area % |
|---|---|---|---|---|---|---|
| 1 | 8.290 | 0.160 | 2299253 | 12994046 | 1506.91 | 98.329 |
| 2 | 8.927 | 0.143 | 11819 | 56297 | 7.75 | 0.426 |
| 3 | 9.313 | 0.147 | 23409 | 119528 | 15.34 | 0.904 |
| 4 | 9.836 | 0.153 | 8540 | 44994 | 5.60 | 0.340 |
| Total | | | | 13214866 | | 100.000 |

TABLE 2

The HPLC data at 254 nm

| Peak# | Ret. Time | USP Width | Height | Area | S/N | Area % |
|---|---|---|---|---|---|---|
| 1 | 8.290 | 0.141 | 521536 | 2489881 | 4431.22 | 98.881 |
| 2 | 8.929 | 0.146 | 1332 | 6766 | 11.32 | 0.269 |
| 3 | 9.314 | 0.148 | 2998 | 15572 | 25.47 | 0.618 |
| 4 | 9.837 | 0.155 | 1055 | 5842 | 8.96 | 0.232 |
| Total | | | | 2518061 | | 100.000 |

Figure 5A:
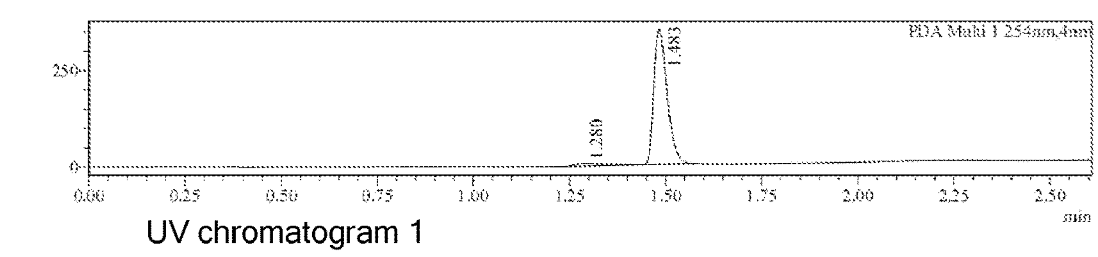
FIG. 5A-C show LC-MS spectrograms of compound TM1 at two detection wavelengths (214 nm and 254 nm) and a total ion chromatogram in anionic mode.
Figure 5B:
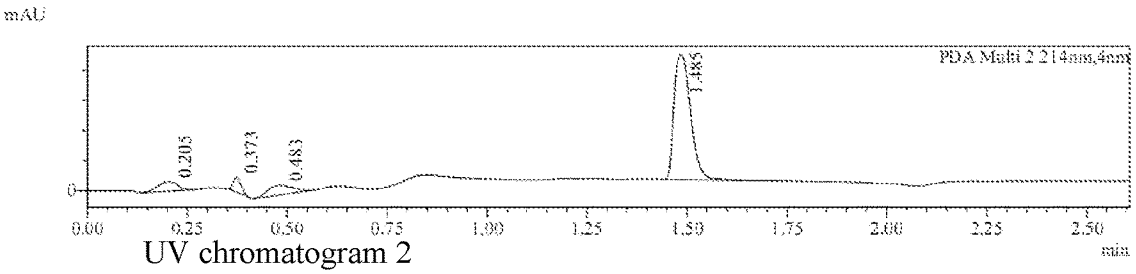
Figure 5C:
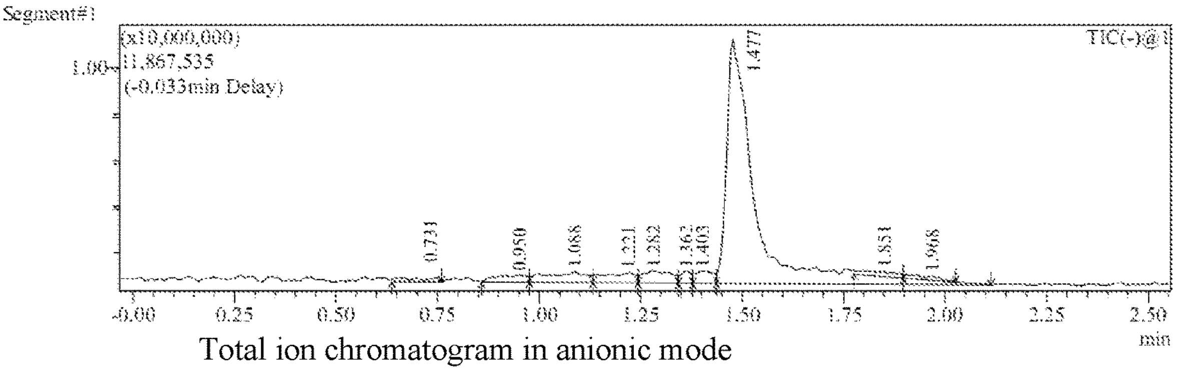

FIG. 5A-C show LC-MS of compound TM1 at two detection wavelengths (254 nm and 214 nm) and a total ion chromatogram in anionic mode, and the LC-MS data at 254 nm and 214 nm are shown in Tables 3 and 4. Herein, LC-MS conditions were as follows: the chromatographic column was Waters SunFire C18 (50×4.6 mm, 5 μm), he flow rate of mobile phase was 2.000 mL/min, the run time was 2.6 min, and the column temperature was 40° C.; the mobile phase A was 0.1 v/v % TFA aqueous solution, and the mobile phase B was 0.1 v/v % TFA in ACN; and the gradient elution program was as follows: holding 5 v/v % mobile phase B for 0.2 min, increasing to 95 v/v % mobile phase B within 1.40 min, holding 95 v/v % mobile phase for 0.9 min, and decreasing to 5 v/v % mobile phase B within 0.01 min.

TABLE 3

The LC-MS data at 254 nm

| Peak# | Ret. Time | Height | Area | Area % |
|---|---|---|---|---|
| 1 | 1.280 | 6497 | 41820 | 4.701 |
| 2 | 1.483 | 350513 | 847787 | 95.299 |
| Total | | 357009 | 889607 | 100.000 |

TABLE 4

The LC-MS data at 214 nm

| Peak# | Ret. Time | Height | Area | Area % |
|---|---|---|---|---|
| 1 | 0.205 | 150950 | 527169 | 7.015 |
| 2 | 0.373 | 248763 | 335507 | 4.465 |
| 3 | 0.483 | 156472 | 705071 | 9.382 |
| 4 | 1.485 | 2078973 | 5947158 | 79.138 |
| Total | | 2635159 | 7514906 | 100.000 |

Figure 6:
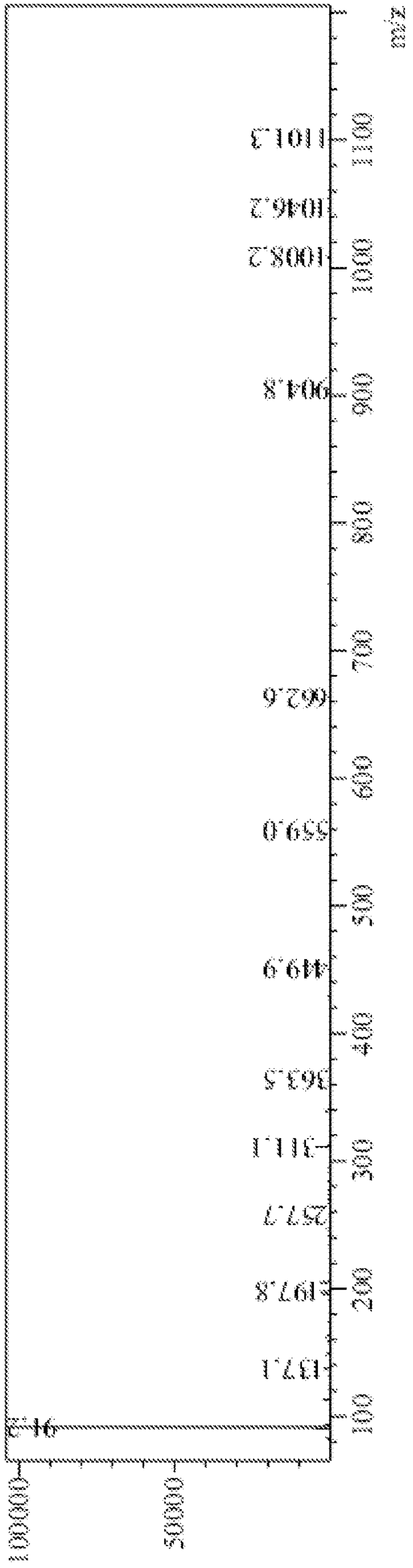
FIG. 6 shows a mass spectrogram of compound TM1.

The mass spectrogram of compound TM1 is shown in FIG. 6. From FIG. 6, the MS m/z (ESI) of the compound TM1 is: 389.0 [M-H].

Test Example 1

In Vitro Liver Microsome Experiment

Experimental group: 136 μL of 50 mM Tris buffer was added to a 1.5 mL centrifuge tube, added with 20 μL of 100 mM aqueous D-glucaro-1,4-lactone solution, 10 μL of 10 mM aqueous magnesium chloride ($MgCl_2$) solution, 10 μL of 40 mg/mL pooled human liver microsomes, and 2 μL of 50 mg/mL alamethicin, respectively, and preincubated on ice for 15 min; 2 μL of 2 mg/mL substrate (3-PBA) was added, and preincubated with 100 mM uridine diphosphate glucuronic acid (UDPGA) solution for 5 min at 37° C.; 20 μL of preincubated UDPGA solution was added to the reaction system to start the reaction, and incubation proceeded. At 0 min and 6 h, 200 μL of glacial acetonitrile was added to the reaction system to terminate the reaction, respectively. The reaction system was vortexed for 1 min and centrifuged at 13,000 r/min for 10 min at 4° C. All supernatants were put in a test tube, nitrogen-blown at 37° C., and reconstituted with 200 μL of methanol. The samples were analyzed and detected by UPLC-MS/MS. The difference between the blank group and the experimental group was only that 3-PBA was not added, and the difference between the control group and the experimental group was only that UDPGA was not added. The initiation factor UDPGA was not added in the blank group, the substrate in the positive control group was carbofuran phenol, and the remaining conditions were the same as those in the experimental group. Herein, magnesium chloride served as a provider of magnesium ions and maintained enzyme activity; alamethicin was intended to punch in liver microsomes, so that the reaction substrate entered liver microsomes for reaction.

Figure 7:
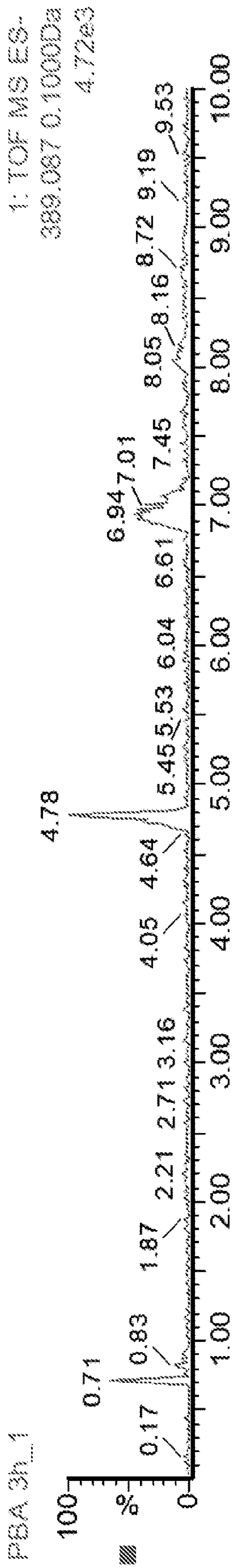
FIG. 7 shows an ultra-high performance liquid chromatography-tandem mass spectrometry (UPLC-MS/MS) result of an experimental group.

The UPLC-MS/MS results of the experimental group are shown in FIG. 7. From FIG. 7, 3-PBA-glucuronic acid metabolite (compound TM1) was detected at 4.78 min after reaction, indicating that 3-PBA, the non-specific metabolite of pyrethroid insecticides, underwent phase II metabolic reaction, and the 3-PBA-glucuronic acid conjugate was compound TM1. The compound TM1, as a poisoning marker, solves the problem of identifying whether pyrethroid pesticides are taken antemortem or exposed postmortem.

Figure 8:
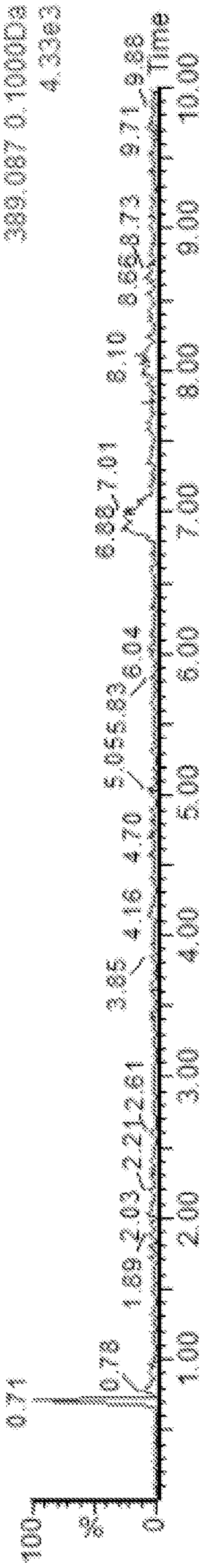
FIG. 8 shows a UPLC-MS/MS result of a blank group.

The UPLC-MS/MS results of the blank group are shown in FIG. 8. From FIG. 8, in the blank group, TM1 was not detected within the same retention time.

Figure 9:
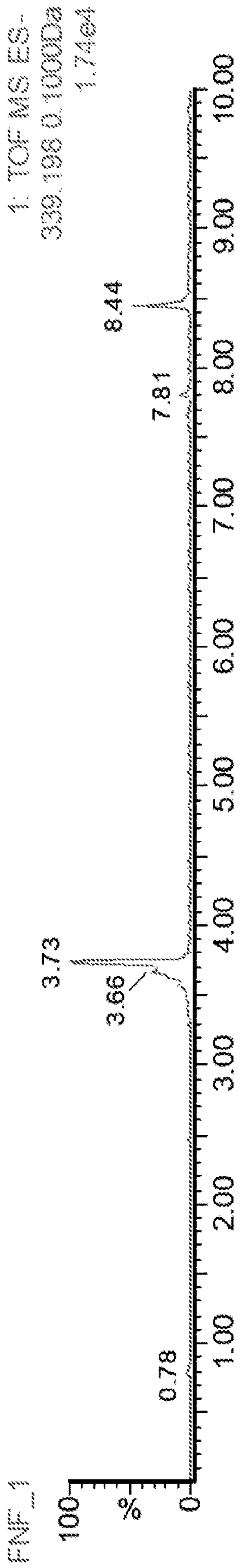
FIG. 9 shows a UPLC-MS/MS result of a positive control group.

The UPLC-MS/MS results of the positive control group are shown in FIG. 9. From FIG. 9, in the positive control group, carbofuran phenol-glucuronic acid conjugate was detected at 3.73 min (the molecular weight in anionic mode was 339).

In conclusion, current forensic identification related to pyrethroid pesticides only focuses on protomers and phase I metabolites. There is no study of phase II metabolites. However, the present disclosure demonstrates the presence of non-specific phase II metabolites of pyrethroid pesticides, and elucidates the chemical structure of phase II metabolites, which is of great importance in the detection of whether one is killed by pyrethroid pesticides.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A preparation method of a 3-phenoxybenzoic acid-glucuronic acid conjugate comprising:

mixing a compound II, a compound III, an organic base, and a coupling reagent with a first organic solvent, and conducting a condensation reaction to yield a compound IV; and mixing the compound IV with a hydrogenation catalyst and a second organic solvent, and conducting a hydrogenation reaction in a hydrogen-atmosphere to yield the 3-phenoxybenzoic acid-glucuronic acid conjugate having a structure represented by formula I;

formula I

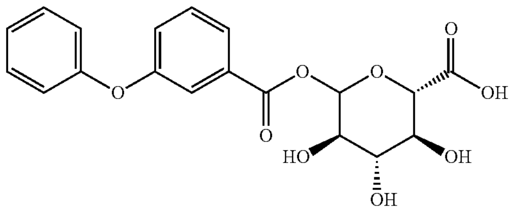

Compound II

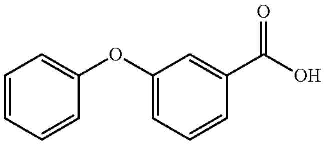

Compound III

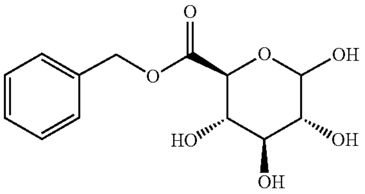

Compound IV

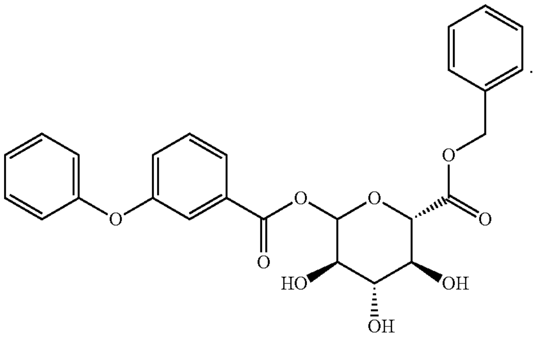

2. The preparation method according to claim 1, wherein a molar ratio of the compound II to the compound II is in a range of 1:(0.3-3).

3. The preparation method according to claim 1, wherein the coupling reagent is at least one selected from the group consisting of 2-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU), N-(3-dimethylaminopropyl)-N'-ethylcarbodiimide hydrochloride, and 1-hydroxybenzotriazole.

4. The preparation method according to claim 1, wherein the first organic solvent is at least one selected from the group consisting of nitrile-based solvents, furan-based solvents, pyridine-based solvents, acyl-based solvents, and alkylogen solvents.

5. The preparation method according to claim 1, wherein the condensation reaction is conducted at a temperature of −10° C. to 80° C. for 0.5-48 h.

6. The preparation method according to claim 2, wherein the condensation reaction is conducted at a temperature of −10° C. to 80° C. for 0.5-48 h.

7. The preparation method according to claim 3, wherein the condensation reaction is conducted at a temperature of −10° C. to 80° C. for 0.5-48 h.

8. The preparation method according to claim 4, wherein the condensation reaction is conducted at a temperature of −10° C. to 80° C. for 0.5-48 h.

9. The preparation method according to claim 1, wherein the hydrogenation catalyst is at least one selected from the group consisting of palladium on carbon, palladium hydroxide, and platinum oxide.

10. The preparation method according to claim 1, wherein the second organic solvent is at least one selected from the group consisting of alcoholic solvents, ester solvents, and alkylogen solvents.

11. The preparation method according to claim 1, wherein the hydrogenation reaction is conducted at a temperature of 0-80° C. for 1-48 h, and hydrogen pressure is 0.1-3 MPa.

12. The preparation method according to claim 9, wherein the hydrogenation reaction is conducted at a temperature of 0-80° C. for 1-48 h, and hydrogen pressure is 0.1-3 MPa.

13. The preparation method according to claim 10, wherein the hydrogenation reaction is conducted at a temperature of 0-80° C. for 1-48 h, and hydrogen pressure is 0.1-3 MPa.

* * * * *